United States Patent
Woodland et al.

(10) Patent No.: US 10,898,422 B2
(45) Date of Patent: *Jan. 26, 2021

(54) METHOD FOR COSMETIC TREATMENT OF KERATINOUS FIBRES COMPRISING SEQUENTIALLY APPLYING A COSMETIC COMPOSITION COMPRISING AT LEAST ONE ORGANIC SILICON COMPOUND IN COMBINATION WITH A COMPOSITION FOR CARING FOR AND/OR WASHING KERATINOUS FIBRES

(75) Inventors: Frédéric Woodland, Paris (FR); Pascale Lazzeri, Levallois-Perret (FR)

(73) Assignee: L'OREAL, Paris (FR)

( * ) Notice: Subject to any disclaimer, the term of this patent is extended or adjusted under 35 U.S.C. 154(b) by 324 days.

This patent is subject to a terminal disclaimer.

(21) Appl. No.: 12/430,168

(22) Filed: Apr. 27, 2009

(65) Prior Publication Data

US 2009/0293899 A1 Dec. 3, 2009

Related U.S. Application Data

(60) Provisional application No. 61/071,656, filed on May 9, 2008.

(30) Foreign Application Priority Data

Apr. 25, 2008 (FR) ..................... 08 52795

(51) Int. Cl.
  *A61K 8/58* (2006.01)
  *A61K 8/365* (2006.01)
  *A61K 8/36* (2006.01)
  *A61Q 5/02* (2006.01)
  *A61Q 5/12* (2006.01)

(52) U.S. Cl.
  CPC ............ *A61K 8/585* (2013.01); *A61K 8/36* (2013.01); *A61K 8/365* (2013.01); *A61Q 5/02* (2013.01); *A61Q 5/12* (2013.01)

(58) Field of Classification Search
  CPC .......... A61K 8/585; A61K 8/36; A61K 8/365; A61Q 5/02; A61Q 5/12
  See application file for complete search history.

(56) References Cited

U.S. PATENT DOCUMENTS

| | | | |
|---|---|---|---|
| 6,953,572 B1 | 10/2005 | Samain et al. | |
| 7,244,420 B1 | 7/2007 | Samain et al. | |
| 2003/0175230 A1 | 9/2003 | Dubief | |
| 2004/0131576 A1* | 7/2004 | Decoster | A61K 8/342 424/70.122 |
| 2004/0138373 A1* | 7/2004 | Hamachi et al. | 524/588 |
| 2006/0110351 A1* | 5/2006 | Koehler | A61K 8/585 424/70.12 |
| 2006/0280716 A1 | 12/2006 | Czech et al. | |
| 2007/0190007 A1 | 8/2007 | Saviades et al. | |
| 2007/0218028 A1* | 9/2007 | Takai et al. | 424/70.12 |
| 2008/0226576 A1* | 9/2008 | Benabdillah | A61Q 5/06 424/70.9 |

FOREIGN PATENT DOCUMENTS

| | | | |
|---|---|---|---|
| EP | 0992528 A2 | | 4/2000 |
| FR | 2 910 275 A1 | | 6/2008 |
| JP | 2006-169163 A | | 6/2006 |
| JP | 2006-169164 | * | 6/2006 |
| WO | WO 01/22925 A1 | | 4/2001 |
| WO | WO 01/22932 A1 | | 4/2001 |
| WO | WO05/97050 | * | 10/2005 |
| WO | 2006/018323 A1 | | 2/2006 |

OTHER PUBLICATIONS

JP2006169164, J-PlatPat Translation (Year: 2006).*
Anonymous, "Auswahl pflegender Wirkstoffe fur einen Haarschaum," SOFW-Journal, vol. 131, No. 3, pp. 38-43 (2005).
Kazuyuki, Y. et al., "Solution Behavior of New Cationic Surfactants Derived from Guerbet Alcohols and their use in Hair Conditioners," International Journal of Cosmetic Science, No. 13, pp. 221-234 (1991).
French Search Report for FR 08/52794, dated Feb. 12, 2009.
French Search Report for FR 08/52795, dated Feb. 13, 2009.
Copending U.S. Appl. No. 12/430,164, filed Apr. 27, 2009.
Restriction Requirement dated Jul. 28, 2011, in co-pending U.S. Appl. No. 12/430,164.
Response to Restriction and Election of Species Requirement filed Sep. 28, 2011, in co-pending U.S. Appl. No. 12/430,164.
Office Action dated Oct. 21, 2011, in co-pending U.S. Appl. No. 12/430,164.
Arkles, B., et al., "Factors Contributing to the Stability of Alkoxysilanes in Aqueous Solution," Silanes and Other Coupling agents, 1992, pp. 91-104.
Non-Final Office Action for copending U.S. Appl. No. 12/430,164, dated Sep. 11, 2012 (now abandoned).
Final Office Action for copending U.S. Appl. No. 12/430,164, dated Jul. 2, 2014 (now abandoned).

(Continued)

*Primary Examiner* — Jeffrey S Lundgren
*Assistant Examiner* — Ibrahim D Bori
(74) *Attorney, Agent, or Firm* — The Marbury Law Group, PLLC

(57) ABSTRACT

A method for the cosmetic treatment of keratinous fibres. A cosmetic composition comprising, in a cosmetically acceptable medium, at least one organic silicon compound comprising at least one basic chemical functional group and at least one hydroxyl or hydrolysable group per molecule, said at least one organic silicon compound being chosen from silanes and siloxanes, and a composition for caring for and/or washing keratinous fibres are applied sequentially in any order. Also disclosed herein is a method for improving the styling effect of a composition for caring for and/or washing keratinous fibres, comprising applying, to the keratinous fibres, the composition for caring for and/or washing keratinous fibres, which is preceded by pre-treating and/or followed by post-treating the keratinous fibres by applying above cosmetic composition.

10 Claims, No Drawings

(56) References Cited

OTHER PUBLICATIONS

Non-Final Office Action for copending U.S. Appl. No. 12/430,164, dated Apr. 6, 2015 (now abandoned).
Final Office Action for copending U.S. Appl. No. 12/430,164, dated Feb. 12, 2016 (now abandoned).
Non-Final Office Action for copending U.S. Appl. No. 12/430,164, dated Apr. 5, 2017 (now abandoned).
Final Office Action for copending U.S. Appl. No. 12/430,164, dated Jul. 16, 2018 (now abandoned).

* cited by examiner

METHOD FOR COSMETIC TREATMENT OF KERATINOUS FIBRES COMPRISING SEQUENTIALLY APPLYING A COSMETIC COMPOSITION COMPRISING AT LEAST ONE ORGANIC SILICON COMPOUND IN COMBINATION WITH A COMPOSITION FOR CARING FOR AND/OR WASHING KERATINOUS FIBRES

This application claims benefit of U.S. Provisional Application No. 61/071,656, filed May 9, 2008, the contents of which are incorporated herein by reference. This application also claims benefit of priority under 35 U.S.C. § 119 to French Patent Application No. FR 0852795, filed Apr. 25, 2008, the contents of which are also incorporated herein by reference.

The present disclosure relates to a method for cosmetic treatment of keratinous fibres, for example, human keratinous fibres, such as the hair, comprising applying to said keratinous fibres, sequentially and in any order: a cosmetic composition comprising, in a cosmetically acceptable medium, at least one organic silicon compound comprising at least one basic chemical functional group and at least one hydroxyl or hydrolysable group per molecule, said at least one organic silicon compound being chosen from silanes and siloxanes, and a composition for caring for and/or washing keratinous fibres, including human keratinous fibres, such as the hair. The present disclosure also relates to a method for improving the styling effect of a composition for caring for and/or washing keratinous fibres comprising applying to the keratinous fibres, the composition for caring for and/or washing keratinous fibres, which is preceded by pre-treating and/or followed by post-treating the keratinous fibres by applying a cosmetic composition comprising, in a cosmetically acceptable medium, at least one organic silicon compound comprising at least one basic chemical functional group and at least one hydroxyl or hydrolysable group per molecule, said at least one organic silicon compound being chosen from silanes and siloxanes.

Hair is generally damaged and embrittled by the action of external atmospheric agents, such as light and bad weather, and by mechanical or chemical treatments, such as brushing, combing, dying, bleaching, perming and/or straightening.

Thus, to overcome those disadvantages, it is now normal to resort to hair care treatments involving the use of care products which can make it possible to condition the hair, for example, by conferring softness, sheen and a natural feel thereon, and to obtain styling effects.

These hair care compositions can, for example, be conditioning shampoos or conditioners which can be provided in the form of gels, hair lotions or more or less thick creams.

Furthermore, it has been found that consumers are increasingly on the lookout for care compositions which may make it possible not only to suitably condition the hair but also to provide satisfactory styling effects.

For example, people having fine or curly hair may be on the lookout for care products that can provide styling effects contributing mass, body and volume to the hair and also defined shape to the curl.

However, conventional care compositions may provide styling effects which can be relatively weak and uneven, for example, in terms of defined curl shape and of volume.

It is known that the introduction of cosmetically active organic compounds, such as silicones and cationic polymers, into care compositions, such as conditioners, can make it possible to confer properties of disentangling, of suppleness and of lightness on the hair. However, the hair styling properties may still remain inadequate.

Thus there exists a real need for a method for the treatment of the hair which does not exhibit at least one of the disadvantages described above, that is, which can provide, for example, satisfactory styling effects.

It has been discovered that it is possible to employ, on keratinous fibres, cosmetic compositions comprising at least one organic silicon compound as defined below in combination with compositions for caring for and/or washing keratinous fibres to obtain the desired properties.

The term "combination" is understood to mean, within the meaning of the present disclosure, that the cosmetic composition comprising at least one organic silicon compound as defined below and the care and/or washing composition can be applied to the keratinous fibres sequentially in any order.

It has been found that the use of a cosmetic composition comprising such organic silicon compounds as disclosed herein in combination with care and/or washing compositions, such as shampoos or conditioners, can result in satisfactory sheathing of the individual hairs, which may thus conferring satisfactory styling effects.

For example, the cosmetic compositions in accordance with the disclosure, used in combination with care and/or washing compositions, can make it possible to confer at least one of volume, body and form retention on the hair style, for example, on fine hair, and also to contribute liveliness to the curl, so as to obtain hair having curls which are better defined in shape.

The styling effects thus obtained can be more marked than those conferred by care and/or washing compositions used alone.

Furthermore, the cosmetic compositions used in supplementing the care and/or washing compositions may make it possible to improve at least one of the styling effects and/or the cosmetic properties conferred by the care and/or washing compositions used alone.

It has been found that the cosmetic compositions used in supplementing the care and/or washing compositions may also make it possible to improve at least one of the sheen, the suppleness and the smoothness of the hair in comparison with the care and/or washing compositions used alone.

Furthermore, in the case where a cosmetic composition comprising at least one organic silicon compound is applied as pretreatment for a care and/or washing composition, the styling effects conferred by this composition may withstand the application of a shampoo or conditioner. This is beneficial in so far as the user may not lose the effect acquired by the pretreatment when he applies a shampoo or a conditioner.

The individual hairs may sometimes also remain better separated and/or may be disentangled more easily with a cosmetic composition in accordance with the disclosure used in combination with a care and/or washing composition.

The term "care composition," or "composition for caring for" is understood to mean, within the meaning of the present disclosure, a nonwashing composition which hopefully does not detrimentally affect in a significant way the colour and/or the integrity of the keratinous fibres while improving appearance and/or the conditioning properties of the said fibres. Accordingly, care composition as defined herein excludes dying, perming, for example, reducing and fixing compositions (oxidizing compositions), and straightening compositions.

According to the present disclosure, the care composition can, for example, comprise less than 4% by weight of anionic surfactants, for further example, less than 2% by weight of anionic surfactants, such as less than 1% by weight of anionic surfactants relative to the total weight of the care composition.

The present disclosure relates to a method for the cosmetic treatment of keratinous fibres, for example, human keratinous fibres, such as the hair, comprising applying to said keratinous fibres, sequentially, in any order: a cosmetic composition comprising, in a cosmetically acceptable medium, at least one organic silicon compound comprising at least one basic chemical functional group and at least one hydroxyl or hydrolysable group per molecule, said at least one organic silicon compound being chosen from silanes and siloxanes, and a composition for caring for and/or washing keratinous fibres, for example, human keratinous fibres, such as the hair; wherein the at least one silane comprises one silicon atom and is chosen from the compounds of formula (I) as defined below; and wherein the at least one siloxane comprises two or three silicon atoms.

In other words, the cosmetic composition comprising, in a cosmetically acceptable medium, at least one organic silicon compound as defined herein is used in supplementing a composition for caring for and/or washing keratinous fibres.

Another aspect of the disclosure is a method for the cosmetic treatment of keratinous fibres comprising applying to said keratinous fibres, sequentially, in any order: a cosmetic composition comprising, in a cosmetically acceptable medium, at least one organic silicon compound comprising at least one basic chemical functional group and at least one hydroxyl or hydrolysable group per molecule, said at least one organic silicon compound being chosen from silanes and siloxanes, and a composition for caring for and/or washing keratinous fibres; further comprising, optionally rinsing after an optional leave-in time or after optionally drying.

Other subject-matters and characteristics, aspects and benefits of the disclosure will become apparent on reading the description and examples which follow.

The at least one organic silicon compound used in the cosmetic composition according to the disclosure is chosen from organosilanes, comprising one silicon atom, and organosiloxanes, comprising two or three silicon atoms, for example two silicon atoms. They additionally comprise at least one basic chemical functional group, for example, just one basic chemical functional group. The basic chemical functional group corresponds to any functional group which confers a basic nature on the silicon compound without harming its solubility in water, for example, an amine functional group, such as a primary, secondary or tertiary amine functional groups. The basic chemical functional group with the silicon compounds according to the disclosure can optionally comprise other functional groups, such as, for example, another amine functional group, an acid functional group or a halogen functional group.

The organic silicon compound or compounds used in the cosmetic composition according to the disclosure additionally comprise at least two hydrolysable or hydroxyl groups per molecule. The hydrolysable groups are, for example, alkoxy, aryloxy or halogen groups. They can also optionally comprise at least one other chemical functional group, such as acid functional groups.

The at least one organosilane used in the cosmetic composition according to the disclosure comprises one silicon atom and is chosen from the compounds of formula (I):

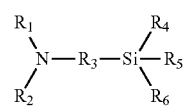

in which:

$R_4$ represents a halogen or an OR' or $R'_1$ group;

$R_5$ represents a halogen or an OR" or $R'_2$ group;

$R_6$ represents a halogen or an OR''' or $R'_3$ group;

$R_1$, $R_2$, $R_3$, R', R", R''', $R'_1$, $R'_2$ and $R'_3$ represent, independently of one another, a saturated or unsaturated, linear or branched hydrocarbon group optionally carrying at least one additional chemical group, $R_1$, $R_2$, R', R" and R''' can also represent, independently of one another, hydrogen; provided that at least two of the $R_4$, $R_5$ and $R_6$ groups respectively denote OR', OR" and OR''', and at least two of the R', R" and R''' groups are other than hydrogen.

For example, the $R_1$, $R_2$, R', $R'_1$, $R'_2$, $R'_3$, R" and R''' groups can be chosen from $C_1$-$C_{12}$ alkyl, $C_6$ to $C_{14}$ aryl, ($C_1$ to $C_8$)alkyl($C_6$ to $C_{14}$)aryl and ($C_6$ to $C_{14}$)aryl($C_1$ to $C_8$)alkyl radicals.

According to at least one embodiment, the at least one siloxane is chosen from the compounds of formula (II):

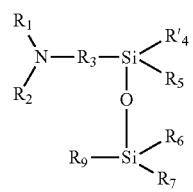

wherein:

$R_5$ represents a halogen or an OR" or $R'_2$ group;

$R_6$ represents a halogen or an OR''' or $R'_3$ group;

$R_1$, $R_2$, $R_3$, R", R''', $R'_2$ and $R'_3$ represent, independently of one another, a saturated or unsaturated, linear or branched hydrocarbon group optionally carrying at least one additional chemical group, $R_1$, $R_2$, R" and R''' can also represent, independently of one another, hydrogen;

$R'_4$ represents a halogen atom or an $OR_{11}$ group;

$R_7$ represents a halogen atom or an $OR_{10}$ or $R''_1$, group;

$R_9$ represents a halogen atom or an $OR_8$, $R''_2$ or $R_3NR_1R_2$ group;

$R''_1$, $R''_2$, $R_8$, $R_{10}$ and $R_{11}$ represent a saturated or unsaturated, linear or branched hydrocarbon group optionally carrying at least one additional chemical group, the groups $R_{11}$, $R_{10}$ and $R_8$ can also represent, independently of one another, hydrogen; provided that at least one of the groups $R_6$, $R_7$ and $R_9$ denotes a halogen atom or, respectively, an OR''', $OR_{10}$ or $OR_8$ group.

For example, the groups $R''_1$, $R''_2$, $R_8$ or $R_{10}$ and $R_{11}$ can be chosen from $C_1$-$C_{12}$ alkyl, $C_6$ to $C_{14}$ aryl, ($C_1$ to $C_8$)alkyl ($C_6$ to $C_{14}$)aryl and ($C_6$ to $C_{14}$)aryl($C_1$ to $C_8$)alkyl radicals.

According to at least one embodiment, the halogen atom is a chlorine atom.

The at least one organic silicon compound used in the cosmetic composition according to the disclosure can be, for example, chosen from the compounds of formula (III):

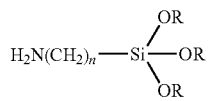

in which the R radicals, which are identical or different, are chosen from $C_1$-$C_6$, such as $C_1$-$C_2$, alkyl radicals and n is an integer ranging from 1 to 6, for example, from 2 to 4.

According to at least one embodiment, the silanes or siloxanes are soluble in water, for example, still soluble at the concentration of 2% by weight, at a concentration of 5% by weight, or at a concentration of 10% by weight in water at a temperature of 25° C.±5° C. and at atmospheric pressure. The term "soluble" is understood to mean the formation of a single macroscopic phase.

According to at least one embodiment, the at least one organic silicon compound present in the cosmetic composition according to the disclosure is (3-aminopropyl)triethoxysilane.

The at least one organic silicon compound can be present in the cosmetic composition according to the disclosure in an amount ranging from 0.1 to 20% by weight, for example, from 1 to 15% by weight, such as from 2.5% to 12% by weight, relative to the total weight of the cosmetic composition.

The cosmetic composition according to the disclosure can comprise at least one organic acid.

The term "organic acid" is understood to mean any nonpolymeric organic compound comprising at least one acid functional group chosen from carboxylic acid, sulphonic acid and phosphoric acid functional groups.

According to at least one embodiment, the at least one organic acid is not a surfactant.

According to at least one embodiment, the molecular weight of the at least one organic acid can be less than 250, for example, less than 200.

The at least one organic acid can be chosen from amino acids.

For example, the at least one organic acid is chosen from acetic acid, propanoic acid, butanoic acid, lactic acid, malic acid, glycolic acid, ascorbic acid, maleic acid, phthalic acid, succinic acid, taurine, tartaric acid, arginine, glycine, glucuronic acid, gluconic acid and citric acid.

In at least one embodiment, the at least one organic acid according to the disclosure is chosen from carboxylic acids.

In at least one other embodiment, the at least one organic acid used in the composition according to the disclosure is chosen from acetic acid, citric acid and, lactic acid.

In the composition, the at least one organic acid can be in the free or salified form.

The at least one organic acid used in the composition according to the present disclosure can be present in an amount, as a free acid, ranging from 0.1 to 10% by weight, for example, from 0.5 to 8% by weight, such as, from 1 to 5% by weight, relative to the total weight of the composition.

The term "cosmetically acceptable medium" is understood to mean a medium compatible with keratinous fibres, such as the hair.

The cosmetically acceptable medium may be composed of water or of a mixture of water and of at least one cosmetically acceptable solvent chosen from lower $C_1$-$C_4$ alcohols, such as ethanol, isopropanol, tert-butanol and n-butanol; and polyols, such as glycerol, propylene glycol and polyethylene glycols.

The cosmetic composition according to the disclosure exhibits a pH ranging from 3 to 11, for example, from 7 to 10.

The cosmetic composition according to the disclosure can additionally comprise at least one conventional additive well known in the art, such as: natural or synthetic thickeners or viscosity regulators; $C_{12}$-$C_{30}$ fatty alcohols; ceramides, fatty esters, such as isopropyl myristate, myristyl myristate, cetyl palmitate and stearyl stearate; mineral, vegetable or synthetic oils, such as α-olefins or palm oil; vitamins or provitamins; cationic or amphoteric polymers; silicones other than the organic silicon compounds according to the disclosure; pH-stabilizing agents; preservatives; and colorants.

According to at least one embodiment, the cosmetic composition according to the disclosure comprises at least one thickening agent.

The at least one thickening agent can be chosen from cellulose thickening agents, for example hydroxyethylcellulose, hydroxypropylcellulose and carboxymethylcellulose, guar gum and its derivatives, for example hydroxypropyl guar, sold by Rhodia under the reference Jaguar HP 105, gums of microbial origin, such as xanthan gum and scleroglucan gum, synthetic thickening agents, such as crosslinked homopolymers of acrylic acid or of acrylamidopropanesulphonic acid, for example Carbomer, or nonionic, anionic, cationic or amphoteric associative polymers, such as the polymers sold under the names Pemulen TR1 or TR2 by Goodrich, Salcare SC90 by Ciba, Aculyn 22, 28, 33, 44 or 46 by Röhm & Haas and Elfacos T210 and T212 by Akzo.

A person skilled in the art will take care to chose the optional additives and their amounts so that they do not harm the properties of the compositions of the present disclosure.

These additives are generally present in the composition according to the disclosure in an amount ranging from 0 to 20% by weight, relative to the total weight of the composition comprising the silanes and/or the siloxanes of the disclosure.

The cosmetic compositions according to the disclosure can be provided in various forms, such as gels, lotions or creams.

The cosmetic composition according to the disclosure and the care and/or washing composition are applied sequentially to keratinous fibres, for example, human keratinous fibres, such as the hair.

According to at least one embodiment, the cosmetic composition according to the disclosure is applied as pre- or as post-treatment for a composition for caring for and/or washing keratinous fibres.

In this case, the cosmetic composition used as pre- or as post-treatment for a composition for caring for and/or washing keratinous fibres can be applied in rinse-out mode or in a leave-in mode, that is, its application is optionally followed by rinsing.

According to at least one embodiment, the cosmetic composition according to the disclosure is used as pretreatment for a composition for caring for and/or washing keratinous fibres The care and/or washing compositions can comprise at least one cationic surfactant.

Mention may be made, as examples of cationic surfactant, of salts of optionally polyoxyalkylenated primary, secondary or tertiary fatty amines and optionally polyoxyalkylenated quaternary ammonium salts.

For example, the cationic surfactants are chosen from optionally polyoxyalkylenated quaternary ammonium salts.

Examples of quaternary ammonium salts include:
those of general formula (IV):

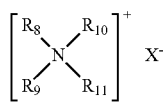
(IV)

wherein the radicals $R_8$ to $R_{11}$, being identical or different, represent a linear or branched aliphatic radical comprising from 1 to 30 carbon atoms or an aromatic radical, such as aryl or alkylaryl. The aliphatic radicals can comprise heteroatoms, such as oxygen, nitrogen, sulphur and halogens.

The aliphatic radicals are, for example, chosen from alkyl, alkoxy, polyoxy($C_2$-$C_6$)-alkylene, alkylamide, ($C_{12}$-$C_{22}$)alkylamido($C_2$-$C_6$)alkyl, ($C_{12}$-$C_{22}$)alkyl acetate and hydroxyalkyl radicals comprising from 1 to 30 carbon atoms; X is an anion chosen from halides, phosphates, acetates, lactates, ($C_2$-$C_6$)alkyl sulphates, and alkyl- or alkylarylsulphonates;

imidazoline quaternary ammonium salts, such as, those of following formula (V):

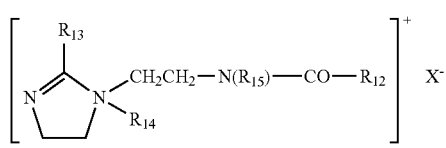
(V)

wherein $R_{12}$ represents an alkenyl or alkyl radical comprising from 8 to 30 carbon atoms, for example derivatives of tallow fatty acids, $R_{13}$ represents a hydrogen atom, a $C_1$-$C_4$ alkyl radical or an alkenyl or alkyl radical comprising from 8 to 30 carbon atoms, $R_{14}$ represents a $C_1$-$C_4$ alkyl radical, $R_{15}$ represents a hydrogen atom or a $C_1$-$C_4$ alkyl radical, and $X^-$ is an anion chosen from halides, phosphates, acetates, lactates, alkyl sulphates, and alkyl- or alkylarylsulphonates. For example, $R_{12}$ and $R_{13}$ denote a mixture of alkenyl or alkyl radicals comprising from 12 to 21 carbon atoms, for example derivatives of tallow fatty acids, $R_{14}$ denotes a methyl radical and $R_{15}$ denotes a hydrogen atom. Such a product is sold, for example, under the name Rewoquat® W 75 by Rewo;

diquaternary ammonium salts of formula (VI):

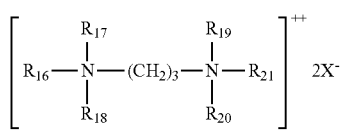
(VI)

wherein $R_{16}$ denotes an aliphatic radical comprising from 16 to 30 carbon atoms, $R_{17}$, $R_{18}$, $R_{19}$, $R_{20}$ and $R_{21}$, which can be identical or different, are chosen from hydrogen or an alkyl radical comprising from 1 to 4 carbon atoms, and X is an anion chosen from halides, acetates, phosphates, nitrates and methyl sulphates. Such diquaternary ammonium salts comprise for example, propanetallowdiammonium dichloride;

quaternary ammonium salts comprising at least one ester functional group, such as those of formula (VII):

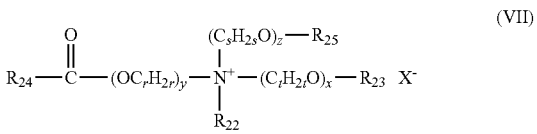
(VII)

wherein:
$R_{22}$ is chosen from $C_1$-$C_6$ alkyl radicals and $C_1$-$C_6$ hydroxyalkyl or dihydroxyalkyl radicals;
$R_{23}$ is chosen from:
the

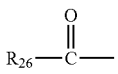

radical
saturated or unsaturated, linear or branched $C_1$-$C_{22}$ hydrocarbon radicals $R_{27}$,
hydrogen,
$R_{25}$ is chosen from:
the

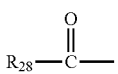

radical
saturated or unsaturated, linear or branched $C_1$-$C_6$ hydrocarbon radicals $R_{29}$,
hydrogen,
$R_{24}$, $R_{26}$ and $R_{28}$, which can be identical or different, are chosen from saturated or unsaturated, linear or branched $C_7$-$C_{21}$, hydrocarbon radicals;
r, s and t, which can be identical or different, are integers ranging from 2 to 6;
y is an integer ranging from 1 to 10;
x and z, which can be identical or different, are integers ranging from 0 to 10;
$X^-$ is an organic or inorganic, simple or complex anion;
with the proviso that the sum x+y+z ranges from 1 to 15, that, when x has a value of 0, then $R_{23}$ denotes $R_{27}$ and that, when z has a value of 0, then $R_{25}$ denotes $R_{29}$.

The $R_{22}$ alkyl radicals can be linear or branched and, and according to at least one embodiment, R22 is linear.

For example, $R_{22}$ denotes a methyl, ethyl, hydroxyethyl or dihydroxypropyl radical and according to at least one embodiment, R22 denotes a methyl or ethyl radical.

According to at least one embodiment, the sum x+y+z ranges from 1 to 10.

When $R_{23}$ is an $R_{27}$ hydrocarbon radical, it can be long having from 12 to 22 carbon atoms or short having from 1 to 3 carbon atoms.

When $R_{25}$ is an $R_{29}$ hydrocarbon radical, it may have from 1 to 3 carbon atoms.

According to at least one embodiment, $R_{24}$, $R_{26}$ and $R_{28}$, which can be identical or different, are chosen from saturated or unsaturated, linear or branched $C_{11}$-$C_{21}$ hydrocarbon radicals, for example, saturated or unsaturated, linear or branched $C_{11}$-$C_{21}$ alkyl and alkenyl radicals.

According to at least one embodiment, x and z, which can identical or different, have values of 0 or 1.

According to at least one embodiment, y is equal to 1.

According to at least one embodiment, r, s and t, which can be identical or different, have values of 2 or 3, for example, r, s and t are equal to 2.

The anion can be for example a halide (chloride, bromide or iodide) or an alkyl sulphate, such as methyl sulphate. However, use may be made of methanesulphonate, phosphate, nitrate, tosylate, an anion derived from an organic acid, such as acetate or lactate, or any other anion compatible with the ammonium comprising an ester functional group.

The anion $X^-$ may be, for example, chloride or methyl sulphate.

Use may be for example, made, in the composition according to the disclosure, of the ammonium salts of formula (VII) in which:
$R_{22}$ denotes a methyl or ethyl radical,
x and y are equal to 1;
z is equal to 0 or 1;
r, s and t are equal to 2;
$R_{23}$ is chosen from:
the

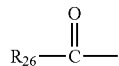

radical
methyl, ethyl or $C_{14}$-$C_{22}$ hydrocarbon radicals,
hydrogen;
$R_{25}$ is chosen from:
the

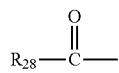

radical
hydrogen atom;
$R_{24}$, $R_{26}$ and $R_{28}$, which can be identical or different, are chosen from saturated or unsaturated, linear or branched $C_{13}$-$C_{17}$ hydrocarbon radicals, for example, saturated or unsaturated, linear or branched $C_{13}$-$C_{17}$ alkyl and alkenyl radicals.

According to at least one embodiment, the hydrocarbon radicals are linear.

Mention may be made, for example, of compounds of formula (VII), such as diacyloxyethyldimethylammonium, diacyloxyethyl(hydroxyethyl)methylammonium, monoacyloxyethyldi(hydroxyethyl)methylammonium, triacyloxyethylmethylammonium or monoacyloxyethyl(hydroxyethyl)dimethylammonium salts (in particular chloride or methyl sulphate), and their mixtures. The acyl radicals for example, have from 14 to 18 carbon atoms and originate for example, from a vegetable oil, such as palm oil or sunflower oil. When the compound comprises several acyl radicals, the latter can be identical or different.

These products are obtained, for example, by direct esterification of triethanolamine, triisopropanolamine, alkyldiethanolamine or alkyldiisopropanolamine, optionally oxyalkylenated, with fatty acids or with mixtures of fatty acids of vegetable or animal origin, or by transesterification of their methyl esters. This esterification is followed by quaternization using an alkylating agent, such as an alkyl halide (for example, methyl or ethyl halide), a dialkyl sulphate (for example, dimethyl or diethyl sulphate), methyl methanesulphonate, methyl para-toluenesulphonate, glycol chlorohydrin or glycerol chlorohydrin.

Such compounds are sold, for example, under the names Dehyquart® by Henkel, Stepanquat® by Stepan, Noxamium® by Ceca or Rewoquat® WE 18 by Rewo-Witco.

The care and/or washing composition can for example, comprise a mixture of quaternary ammonium mono-, di- and triester salts with a predominance by weight of diester salts.

Use may be made, as mixture of ammonium salts, for example, of the mixture comprising from 15 to 30% by weight of acyloxyethyldi(hydroxyethyl)methylammonium methyl sulphate, from 45 to 60% by weight of diacyloxyethyl(hydroxyethyl)methylammonium methyl sulphate and from 15 to 30% by weight of triacyloxyethylmethylammonium methyl sulphate, the acyl radicals having from 14 to 18 carbon atoms and originating from palm oil which is optionally partially hydrogenated.

Use may also be made of the ammonium salts comprising at least one ester functional group described in U.S. Pat. No. 4,874,554 and U.S. Pat. No. 4,137,180.

According to at least one embodiment, quaternary ammonium salts of formula (IV) can be tetraalkylammonium chlorides, for example, dialkyldimethylammonium or alkyltrimethylammonium or alkylaralkyldimethylammonium chlorides in which the alkyl radical comprises from 12 to 22 carbon atoms, such as behenyltrimethylammonium chloride, distearyldimethylammonium chloride, cetyltrimethylammonium chloride or benzyl-dimethylstearylammonium chloride. According to at least one embodiment, quaternary ammonium salts of formula (IV) can be palmitamidopropyltrimethylammonium chloride or stearamidopropyldimethyl(myristyl acetate)ammonium chloride, sold under the name Ceraphyl® 70 by Van Dyk.

For example, the at least one cationic surfactant used in the care and/or washing composition can be chosen from behenyltrimethylammonium chloride and cetyltrimethylammonium chloride.

The at least one cationic surfactant can, for example, be present in an amount ranging from 0.1 to 6% by weight of cationic surfactants, for further example, from 0.5 to 3% by weight, relative to the total weight of the care and/or washing composition and relative to the total weight of the care composition.

The care and/or washing compositions can also comprise at least one surfactant chosen from anionic, amphoteric and nonionic surfactants.

For example, the washing compositions comprise at least one anionic surfactant.

The at least one anionic surfactant which can be used in the compositions of the disclosure is chosen for example, from the salts, for example, alkali metal salts, such as sodium salts, ammonium salts, amine salts, aminoalcohol salts or alkaline earth metal salts, for example magnesium salts, of the following types: alkyl sulphates, alkyl ether sulphates, alkylamido ether sulphates, alkylaryl polyether sulphates, monoglyceride sulphates, alkylsulphonates, alkylamidesulphonates, alkylarylsulphonates, α-olefinsulphonates, paraffinsulphonates, alkyl sulphosuccinates, alkyl ether sulphosuccinates, alkylamide sulphosuccinates, alkyl sulphoacetates, acylsarcosinates and acylglutamates, the alkyl and acyl groups of all these compounds comprising from 6 to 24 carbon atoms and the aryl group for example, denoting a phenyl or benzyl group.

Use may also be made of $C_{6-24}$ alkyl monoesters of polyglycosidedicarboxylic acids, such as alkyl glucosidecitrates, alkyl polyglycosidetartrates and alkyl polyglycosidesulphosuccinates, alkyl sulphosuccinamates, acylisethionates and N-acyltaurates, the alkyl or acyl group of all these compounds comprising from 12 to 20 carbon atoms.

Another group of anionic surfactant agents which can be used in the compositions of the present disclosure is that of the acyl lactylates, the acyl group of which comprises from 8 to 20 carbon atoms.

In addition, mention may also be made of alkyl-D-galactosideuronic acids and their salts, and also polyoxylkylenated $(C_{6-24})$alkyl ether carboxylic acids, polyoxyalkylenated $(C_{6-24})$alkyl$(C_{6-24})$aryl ether carboxylic acids, polyoxyalkylenated $(C_{6-24})$alkylamido ether carboxylic acids and their salts, for example, those comprising from 2 to 50 ethylene oxide units, and their mixtures.

Use may be, for example, made of alkyl sulphates, alkyl ether sulphates and their mixtures, for example, in the form of alkali metal, alkaline earth metal, ammonium, amine or aminoalcohol salts.

The at least one anionic surfactant can be present in an amount of at least 4% by weight, relative to the total weight of the washing composition.

The at least one anionic surfactant can, for example, be present in an amount ranging from 0.01 to 50% by weight, such as, from 0.1 to 20% by weight, relative to the total weight of the care and/or washing composition.

According to at least one embodiment, the care composition does not comprise anionic surfactants.

Examples of additional nonionic surfactants which can be used in the compositions of the present disclosure are described, for example, in "Handbook of Surfactants" by M. R. Porter, published by Blackie & Son (Glasgow and London), 1991, pp 116-178. They are chosen, for example, from polyethoxylated, polypropoxylated or polyglycerolated fatty alcohols, α-diols, $(C_{1-20})$alkylphenols and acids having a fatty chain comprising, for example, from 8 to 18 carbon atoms, it being possible for the number of ethylene oxide or propylene oxide groups to range, for example, from 2 to 50 and it being possible for the number of glycerol groups to range for example, from 2 to 30.

Mention may also be made of condensates of ethylene oxide and of propylene oxide with fatty alcohols; polyethoxylated fatty amides for example, having from 2 to 30 ethylene oxide units, polyglycerolated fatty amides comprising on average from 1 to 5 glycerol groups and for example, from 1.5 to 4, ethoxylated sorbitan fatty acid esters having from 2 to 30 ethylene oxide units, sucrose fatty acid esters, polyethylene glycol fatty acid esters, $(C_{6-24}$ alkyl) polyglycosides, N—$(C_{6-24}$ alkyl)glucamine derivatives or amine oxides, such as $(C_{10-14}$ alkyl)amine oxides or N—$(C_{10-14}$ acyl)aminopropylmorpholine oxides.

When they are present, the amount of the at least one additional nonionic surfactant is for example, in the range from 0.01 to 20% by weight, such as from 0.1 to 10% by weight, relative to the total weight of the care and/or washing composition.

The amphoteric or zwitterionic surface-active agents which can be used in the care and/or washing composition can for example, be chosen from aliphatic secondary or tertiary amine derivatives in which the aliphatic group is a linear or branched chain comprising from 8 to 22 carbon atoms and comprising at least one anionic group, such as, a carboxylate, sulphonate, sulphate, phosphate or phosphonate group. Exemplary mention may be made of $(C_{8-20})$alkyl betaines, sulphobetaines, $(C_{8-20}$ alkyl) amido$(C_{6-8}$ alkyl) betaines or $(C_{8-20}$ alkyl) amido$(C_{6-8}$ alkyl) sulphobetaines.

Mention may be made, among amine derivatives, of the products sold under the name Miranol®, such as described in U.S. Pat. No. 2,528,378 and U.S. Pat. No. 2,781,354 and classified in the CTFA dictionary, 3rd Edition, 1982, under the names Amphocarboxyglycinate and Amphocarboxypropionate with the respective structures (A) and (B):

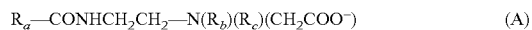

wherein:

$R_a$ represents an alkyl group derived from an acid $R_a$—COOH present in hydrolyzed coconut oil or a heptyl, nonyl or undecyl group, $R_b$ represents a β-hydroxyethyl group, and $R_c$ represents a carboxymethyl group; and

wherein:

B represents —CH$_2$CH$_2$OX',

B' represents —(CH$_2$)$_z$—Y', with z=1 or 2,

X' represents the —CH$_2$CH$_2$—COOH group or a hydrogen atom,

Y' represents —COOH or the —CH$_2$—CHOH—SO$_3$H group, $R_a'$ represents an alkyl group of an acid $R_a'$—COOH present in hydrolyzed coconut oil or in hydrolyzed linseed oil, an alkyl group, for example, a $C_{17}$ alkyl group and its isoform, or an unsaturated $C_{17}$ group.

These compounds are classified in the CTFA dictionary, 5th Edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

Exemplary mention may be made of the cocoamphodiacetate sold by Rhodia under the trade name Miranol® C2M Concentrate.

Use may be made, among the amphoteric or zwitterionic surfactants mentioned above, of $(C_{8-20}$ alkyl) betaines, $(C_{8-20}$ alkyl) amido$(C_{6-8}$ alkyl) betaines and their mixtures.

When they are present, the amount of the amphoteric or zwitterionic surfactant or surfactants may be within the range from 0.01 to 20% by weight, for example, from 0.1 to 10% by weight, relative to the total weight of the care and/or washing composition.

The care and/or washing compositions can be used for the washing of keratinous fibres, such as the hair, for example as shampoos, such as conditioning shampoos, or also for the conditioning of keratinous fibres, for example as conditioners.

According to at least one embodiment, the care compositions can be used as a before conditioner or a conditioner.

In the case of conditioning shampoos, the composition comprises at least one anionic surfactant.

According to at least one embodiment, the care and/or washing compositions may be rinse-out or leave-in conditioners for example, comprising at least one cationic surfactant.

The care and/or washing compositions can additionally comprise at least one conventional additive well known in the art, such as natural or synthetic thickeners or viscosity regulators; ceramides; silicones other than the organic silicon compounds used in the pre- or post-treatment composition; oily fatty esters, such as isopropyl myristate; mineral, vegetable or synthetic oils, such as α-olefins; vitamins or provitamins; cationic or amphoteric polymers; pH-stabilizing agents; preservatives; and colorants.

Another subject-matter of the present disclosure is a method for the cosmetic treatment of keratinous fibres, including human keratinous fibres, such as the hair, comprising applying sequentially, in any order: a cosmetic composition comprising, in a cosmetically acceptable medium, at least one organic silicon compound comprising at least one basic chemical functional group and at least one hydroxyl or hydrolysable group per molecule, said at least one organic silicon compound being chosen from silanes and siloxanes, and a composition for caring for and/or washing keratinous fibres; further comprising, optionally rinsing after an optional leave-in time or after an optional drying.

This treatment method can be employed on natural keratinous fibres or fibres which have been subjected to a cosmetic treatment, such as perming, dying, bleaching or straightening.

According to at least one embodiment, the treatment method comprises applying to the keratinous fibres, as a pretreatment, the cosmetic composition as disclosed herein, optionally rinsing after an optional leave-in time or after an optional drying; then applying the composition for caring for and/or washing keratinous fibres, and optionally rinsing after an optional leave-in time or after an optional drying.

According to at least one embodiment, the care and/or washing composition is a rinse-out composition.

According to at least one embodiment, the treatment method comprises applying to the keratinous fibres the composition for caring for and/or washing keratinous fibres, optionally rinsing after an optional leave-in time or after an optional drying; then applying, as a post-treatment, the cosmetic composition, and optionally rinsing after an optional leave-in time or after an optional drying.

According to at least one embodiment, the pretreatment compositions are not rinse-out compositions, that is, their application is not followed by rinsing.

According to at least one embodiment, the pretreatment is carried out with the cosmetic composition comprising at least one organic silicon compound.

The leave-in time of the pre- or post-treatment composition and of the care and/or washing composition can range from a few seconds to 60 minutes and for example, from 30 seconds to 15 minutes.

The pre- or post-treatment composition and the care and/or washing composition may be applied several times.

The leave-in time of the combination on keratinous fibres can range from a few seconds to 60 minutes and for example, from 30 seconds to 15 minutes.

In all cases, the optional drying can be carried out with a hood dryer, with a hand-held hairdryer and/or with a smoothing iron.

The examples which follow is intended to illustrate the disclosure without, however, limiting the scope thereof.

EXAMPLES

Example I

In the following example, the styling effects obtained on fine hair and on curly hair were evaluated with a composition in accordance with the disclosure which was used as pretreatment for a conditioner.

1. Composition Tested

A composition A was prepared from the ingredients shown in Table I below, the amounts of which were expressed as percent by weight, with respect to the total weight of the composition.

TABLE I

| Composition A | |
| --- | --- |
| 3-Aminopropyltriethoxysilane | 10 |
| Lactic acid | 4 |
| Water | q.s. for 100 |

2. Procedure 20 models (10 fine hair and 10 curly hair) applied the composition A to their hair. After a leave-in time of 30 seconds without intermediate rinsing, the models applied a conditioner, ULTRADOUX® Cerise et Nacre, comprising, as active ingredients, 0.8% AM of cetyltrimethylammonium chloride, 1% by weight of quaternium 80 and 1.35% by weight of dipalmitoylethylhydroxyethylammonium methosulphate. After 30 seconds, the hair was rinsed and dried.

3. Results

The 10 testers with fine hair unanimously considered the hair to be of greater volume than in the context of the use of a conditioner without use of the pretreatment.

With regard to the 10 testers with curly hair, 7 out of 10 found that the curls of hair were better defined in shape and 8 out of 10 found the curls of hair to be livelier.

Example II

In the following example, the styling effects obtained on fine hair and on curly hair were evaluated with a composition in accordance with the disclosure which was used as pretreatment for a shampoo.

1. Composition Tested

A composition B and a composition C were prepared from the ingredients shown in Table II below, the amounts of which were expressed as percent by weight, relative to the total weight of the composition.

TABLE II

| | Composition B | Composition C |
| --- | --- | --- |
| 3-Aminopropyltriethoxysilane [1] | 10 | — |
| Lactic acid | 4 | — |
| Hydroxyethylcellulose | 0.7 | 0.7 |
| Potassium hydroxide | — | q.s. pH composition B = 9 |
| Fragrance, colorants | q.s. | q.s. |
| Water | q.s. for 100 | q.s. for 100 |

Composition B exhibited a pH value equal to 9.

2. Procedure 6 g of composition B were applied to six models on one side of the head and 6 g of composition C were applied to the other side of the head, as comparison. After a leave-in time of 30 seconds and without intermediate rinsing, 6 g of Elsève Multivitamin 2-in-1 shampoo, which comprised 15.5% of sodium lauryl ether sulphate and 2.4% by weight of coco betaine, were applied on both sides. The shampoo was subsequently rinsed out and the hair dried.

3. Results

A panel of experts subsequently carried out a comparative evaluation, a grade ranging from 1 to 5 being assigned. The means of these grades were combined in Table III below.

TABLE III

| | Sensory evaluation | Composition B + Shampoo | Composition C + Shampoo |
|---|---|---|---|
| During rinsing | Smoothness | 3.3 | 2.4 |
| | Suppleness | 3.4 | 2.6 |
| On wet hair | Disentangling | 4.1 | 3.3 |
| | Smoothness | 3.3 | 2.8 |

These results showed that, on wet hair, the hair was smoother and disentangled more easily with composition B, in accordance with the disclosure, used as pretreatment for a shampoo, than with a composition C, not in accordance with the disclosure, used as pretreatment for a shampoo.

These results also showed that, during the rinsing of the shampoo, the hair was smoother and more supple with composition B, in accordance with the disclosure, which was used as pretreatment for a shampoo, than with a composition C, not in accordance with the disclosure, used as pretreatment for a shampoo.

Example III

In the following example, the styling effects and the cosmetic properties obtained with a composition used as pretreatment for a conditioner were compared with those obtained with a conditioner in which the pretreatment was replaced by a simple treatment with water.
1. Composition Tested
A composition A identical to that described in Example I, Table I was prepared.
2. Procedures
6 g of composition A were applied to one side of the head of six models, whose hair had been washed, and 6 g of water were applied to the other half of the head, as comparison. After a leave-in time of 30 seconds and without intermediate rinsing, 6 g of L'Oréal PROFESSIONNEL LUMI CARE conditioner, which comprised 0.8% AM of cetyltrimethylammonium chloride, 1% by weight of quaternium 80 and 1.35% by weight of dipalmitoylethylhydroxyethylammonium methosulphate, were applied on both sides. The conditioner was subsequently rinsed out and the hair dried. This application was repeated three times in succession at intervals of 48 h over a period of 5 days. The evaluations were carried out during this third application.
3. Results
A panel of experts subsequently carried out a comparative evaluation, a grade ranging from 1 to 5 being assigned. The means of these grades were combined in Table IV below.

TABLE IV

| | Sensory evaluation | Composition A + Conditioner | Water + Conditioner |
|---|---|---|---|
| Wet hair | Suppleness | 3.1 | 2.4 |
| Dry hair | Sheen | 3.7 | 3.3 |
| | Visual smoothness | 3.4 | 2.8 |
| | Smoothness to the touch | 3.9 | 3.3 |

These results showed that, on wet hair, the hair was more supple with composition A, used as pretreatment for a conditioner, than with a simple pretreatment with water.

These results also showed that, on dry hair, the hair exhibited greater sheen, was smoother to the touch and was smoother visually with composition A, used as pretreatment for a conditioner, than with a simple pretreatment with water.

In addition, it was found that the hair was coated more homogeneously, which conferred greater volume on the hair.

Example IV

In the following example, the styling effects and the cosmetic properties obtained with a composition used as post-treatment for a conditioner in accordance with the disclosure were compared with those obtained with a conditioner used with a post-treatment composed solely of water.
1. Composition Tested
A composition A identical to that described in Example I, Table I was prepared.
2. Procedures
6 g of L'Oréal PROFESSIONNEL LUMI CARE conditioner, which comprised 0.8% AM of cetyltrimethylammonium chloride, 1% by weight of quaternium 80 and 1.35% by weight of dipalmitoylethylhydroxyethylammonium methosulphate, were applied on both sides to six models whose hair had been washed. After a leave-in time of 30 seconds and without intermediate rinsing, 6 g of composition A were applied on one side of the head and 6 g of water were applied on the other side of the head, as comparison. The hair was subsequently rinsed and then dried. This application was repeated three times in succession at intervals of 48 h over a period of 5 days. The evaluations were carried out during this third application.
3. Results
A panel of experts subsequently carried out a comparative evaluation, a grade ranging from 1 to 5 being assigned with regard to certain criteria. The means of these grades were combined in Table V below.

TABLE V

| | Sensory evaluation | Conditioner + Composition A | Conditioner + Water |
|---|---|---|---|
| Wet hair | Separation | 2.5 | 1.8 |
| | Suppleness | 3.5 | 2.9 |
| | Smooth to the touch | 3.2 | 2.5 |
| Dry hair | Separation | 2.7 | 2.1 |

These results showed that, with regard to wet hair, the individual hairs showed greater separation and were better coated with composition A, used as post-treatment for a conditioner, than with a simple post-treatment with water.

These results also showed that, with regard to dry hair, the hair was more supple and smoother to the touch and the individual hairs showed greater separation with composition A, used as post-treatment for a conditioner, than in the absence of this post-treatment.

In addition, it was found that composition A, used as post-treatment for a conditioner, conferred greater volume on the hair than with a simple post-treatment with water.

What is claimed is:
1. A method for the conditioning and/or styling of keratinous fibres comprising:
applying to said keratinous fibres:
(a) a cosmetic composition comprising, in a cosmetically acceptable medium,
(i) (3-aminopropyl)triethoxysilane in an amount ranging from 0.1 to 12% by weight, relative to the total weight of the composition and
(ii) at least one carboxylic organic acid chosen from lactic acid, citric acid and acetic acid in an amount ranging from 0.1 to 5% by weight relative to the total weight of the cosmetic composition, and (b) a non-washing composition for caring for keratinous fibres, the non-washing composition comprising less than 4% by weight of anionic surfactants, and comprising at least one cationic surfactant chosen from quaternary ammonium, salts selected from dialkyldimethylammonium or alkyltrimethyl-ammonium chlorides in which the alkyl radical comprises approximately from 12 to 22 carbon atoms, or from palmitamidopropyltrimethylammonium chloride or stearamidopropyldimethyl(myristyl acetate)ammonium chloride in an amount ranging from 0.5 to 6% by weight relative to the total weight of the non-washing composition wherein the cosmetic composition (a) is applied as a pre-treatment composition before the non-washing composition for caring for keratinous fibres (b), and wherein composition (a) is not rinsed from the keratinous fibres prior to applying composition (b).

2. The method according to claim 1, wherein the (3-aminopropvl)triethoxvsilane is present in an amount ranging from 2.5 to 12% by weight, relative to the total weight of the composition.

3. The method according to claim 1, wherein the at least one organic acid is present in an amount ranging from 1 to 5% by weight relative to the total weight of the cosmetic composition.

4. The method according to claim 1, wherein the non-washing composition for caring for keratinous fibres is a conditioner.

5. The method according to claim 1, further comprising, rinsing the keratinous fibers after leaving-in the cosmetic composition and the non-washing composition for caring for keratinous fibres for a period of time.

6. A method for the conditioning and/or styling of keratinous fibres comprising:

applying to said keratinous fibres:

(a) a cosmetic composition comprising, in a cosmetically acceptable medium, (i) (3-aminopropyl)triethoxysilane in an amount ranging from 0.1 to 12% by weight, relative to the total weight of the composition and (ii) at least one carboxylic organic acid chosen from lactic acid, citric acid and acetic acid in an amount ranging from 0.1 to 5% by weight relative to the total weight of the cosmetic composition, and (b) a non-washing composition for caring for keratinous fibres, the non-washing composition comprising less than 4% by weight of anionic surfactants, and comprising at least one cationic surfactant quaternary ammonium salt selected from dialkyldimethylammonium or alkyltrimethylammonium chlorides in which the alkyl radical comprises approximately from 12 to 22 carbon atoms, or from palmitamidopropyltrimethylammonium chloride or stearamidopropyldimethyl(myristyl acetate)ammonium chloride in an amount ranging from 0.5 to 6% by weight relative to the total weight of the non-washing composition, wherein the cosmetic composition (a) is applied as a post-treatment composition after the non-washing composition for caring for keratinous fibres (b), and wherein composition (b) is not rinsed from the keratinous fibres prior to applying composition (a).

7. The method according to claim 6, wherein the 3-aminopropyl)triethoxysilane is present in an amount ranging from 2.5 to 12% by weight, relative to the total weight of the composition.

8. The method according to claim 6, wherein the at least one organic acid is present in an amount ranging from 1 to 5% by weight relative to the total weight of the cosmetic composition.

9. The method according to claim 6, wherein the non-washing composition for caring for keratinous fibres is a conditioner.

10. The method according to claim 6, further comprising, rinsing the keratinous fibers after leaving-in the cosmetic composition and the composition for caring for keratinous fibres for a period of time.

* * * * *